United States Patent
Hutchenson et al.

(10) Patent No.: US 10,087,393 B2
(45) Date of Patent: *Oct. 2, 2018

(54) RECOVERY OF PERFLUORINATED POLYETHER OILS FROM GREASE MATRICES INCORPORATING EXTRACTION AIDS BY CARBON DIOXIDE EXTRACTION

(71) Applicant: THE CHEMOURS COMPANY FC, LLC, Wilmington, DE (US)

(72) Inventors: Keith W Hutchenson, Lincoln University, PA (US); Sharon Ann Libert, Hockessin, DE (US); Jon Lee Howell, Bear, DE (US); Xian Liang, Moorestown, NJ (US); Val Krukonis, Lexington, MA (US); Hans Schonemann, Newburyport, MA (US)

(73) Assignee: THE CHEMOURS COMPANY FC, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/109,216

(22) PCT Filed: Dec. 23, 2014

(86) PCT No.: PCT/US2014/072194
§ 371 (c)(1),
(2) Date: Jun. 30, 2016

(87) PCT Pub. No.: WO2015/105685
PCT Pub. Date: Jul. 16, 2015

(65) Prior Publication Data
US 2016/0319216 A1    Nov. 3, 2016

Related U.S. Application Data

(60) Provisional application No. 61/924,461, filed on Jan. 7, 2014.

(51) Int. Cl.
*C10M 175/00* (2006.01)
*B01D 15/12* (2006.01)
*B01D 11/04* (2006.01)
*C07C 41/38* (2006.01)
*C08G 65/30* (2006.01)

(52) U.S. Cl.
CPC ..... *C10M 175/005* (2013.01); *B01D 11/0403* (2013.01); *B01D 11/0407* (2013.01); *B01D 11/0492* (2013.01); *B01D 15/12* (2013.01); *C07C 41/38* (2013.01); *C08G 65/30* (2013.01); *C10M 175/0083* (2013.01); *C10M 2213/06* (2013.01); *C10M 2213/062* (2013.01); *C10M 2213/0606* (2013.01); *C10N 2230/08* (2013.01); *C10N 2250/10* (2013.01)

(58) Field of Classification Search
None
See application file for complete search history.

(56) References Cited

U.S. PATENT DOCUMENTS

| 4,941,987 A * | 7/1990 | Strepparola | C08G 65/007 508/128 |
| 4,978,649 A | 12/1990 | Surovikin et al. | |
| 6,670,309 B2 * | 12/2003 | Chiba | B01D 15/00 208/18 |
| 9,371,498 B2 * | 6/2016 | Bongaerts | B01J 20/24 |
| 2003/0073588 A1 * | 4/2003 | Howell | C10M 105/74 508/182 |
| 2003/0232220 A1 * | 12/2003 | Yatsue | C10M 107/38 428/835.8 |
| 2004/0092406 A1 | 5/2004 | Osawa | |
| 2011/0206853 A1 * | 8/2011 | Riganti | C10M 107/38 427/358 |
| 2013/0237462 A1 | 9/2013 | Valsecchi | |

FOREIGN PATENT DOCUMENTS

| DE | 19739659 | 3/1999 | |
| WO | WO2012104104 A1 * | 8/2012 | ............. B01D 11/02 |

OTHER PUBLICATIONS

Scialdone et al. ("Effective recovery of perfluoropolyether surfactants from PVDF and PTFE by supercritical carbon dioxide extraction", The Journal of Supercritical Fluids, vol. 39, 2007, pp. 347-353).*
Kirk-Othmer Encycl. of Chem. Technology, 4th Ed., vol. 23, pp. 1-29 (Referenced in the specification as pp. 452-477).
International Search Report and Written Opinion, PCT/2014/072194, dated Mar. 24, 2015.

* cited by examiner

*Primary Examiner* — Rosalynd Ann Keys

(57) ABSTRACT

This disclosure relates to a process for extracting a perfluoropolyether. The process involves: (a) contacting a solvent comprising a liquid or supercritical carbon dioxide with a lubricating grease comprising a thickener, an extraction aid material, and the perfluoropolyether in an extraction zone to form an extraction solution comprising an extracted perfluoropolyether; and (b) recovering the extracted perfluoropolyether from the extraction solution; wherein the recovered extracted perfluoropolyether comprises no more than about 2 wt % of the thickener.

20 Claims, 3 Drawing Sheets

RECOVERY OF PERFLUORINATED POLYETHER OILS FROM GREASE MATRICES INCORPORATING EXTRACTION AIDS BY CARBON DIOXIDE EXTRACTION

BACKGROUND

Field of the Disclosure

The present disclosure relates to a process for extracting and recovering a perfluoropolyether from a lubricating grease.

Description of Related Art

Perfluoropolyether (PFPE) oils are highly valued for properties including high-temperature performance, non-flammability, chemical inertness, superior stability and lubricity. Lubricating grease compounds, which possess similar properties, are created by combining the PFPE oil with a variety of thickeners and optionally other additives to meet the requirements of different applications.

Lubricating greases are manufactured so that the PFPE oil and the thickeners and other additives do not easily separate. This is extremely important in lubrication applications that experience high temperatures or high mechanical loads. An example of this requirement is in the aerospace industry which has adopted a military specification MIL-PRF-27617G that limits the amount of oil separation for various grades of grease. MIL-PRF-27617G Type II grease has a maximum allowance of oil separation of 15.0% when the grease is exposed to a temperature of 204° C. for a total of 30 hours. The oil separation is measured according to ASTM Method D6184 Standard Test Method for Oil Separation from Lubricating Grease.

Manufacturers that produce the lubricating grease compounds and the OEMS that consume the lubricating grease compounds generate waste streams of grease. The grease waste occurs during equipment cleanouts or during product transitions or during incomplete grease product removal from a package or other process steps that are common to manufacturing operations. The PFPE oil in the grease waste stream is not affected by contact with the additives or by the time in the waste stream, and the PFPE oil retains all of its valuable properties.

Therefore, there is a need to develop a cost-effective and environmentally-friendly process that is capable of separating the PFPE oil from the grease and recovering the oil for use.

BRIEF SUMMARY OF THE DISCLOSURE

The present disclosure provides a process for extracting a perfluoropolyether from a lubricating grease. The process comprises: (a) contacting a solvent comprising a liquid or supercritical carbon dioxide with the lubricating grease comprising a thickener, an extraction aid material, and the perfluoropolyether in an extraction zone to form an extraction solution comprising an extracted perfluoropolyether; and (b) recovering the extracted perfluoropolyether from the extraction solution; wherein the recovered extracted perfluoropolyether comprises no more than about 2 wt % of the thickener.

BRIEF DESCRIPTION OF THE FIGURES

Embodiments are illustrated in the accompanying figures to improve understanding of concepts as presented herein.

Figure 1:
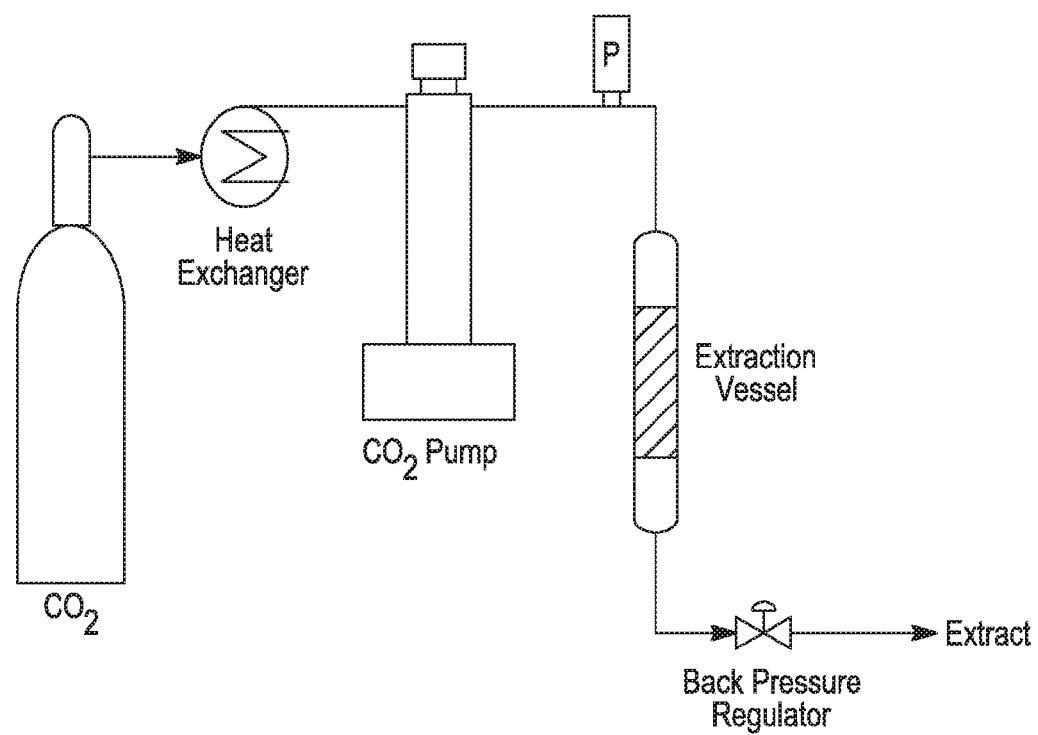
FIG. 1 includes as illustration the extraction process flowsheet of custom high-pressure extraction apparatus.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

The term "wt %", as used herein, means weight percent.

The term "extraction", "extracted", or "extracting", as used herein, means a physical or chemical method of removing one or more components from a substrate by means of a solvent.

The term "extraction aid", as used herein, means an inert material that can be incorporated into the perfluoropolyether lubricating grease which facilitates the extraction process, for example, through material handling and/or by improving the flow distribution of the solvent in the extraction vessel under the particular pressure and flow conditions of the extraction process.

The term "extracted perfluoropolyether", as used herein, means a perfluoropolyether that has been separated from the lubricating grease through extraction processes of this invention.

The term "lubricating grease", as used herein, means the grease receiving the extraction processes of this invention to recover the PFPE oil contained therein. Typically, the lubricating grease comprises PFPE and one or more thickeners and other additives (if present, e.g., anti-corrosion additives) used in making such grease. Moreover, prior to the extraction process at least some extraction aid material is added to the lubricating grease to further aid in the extraction process.

The term "yield of the extracted perfluoropolyether", as used herein, means the amount of the extracted PFPE compared to the total amount of PFPE contained in the lubricating grease prior to extraction.

Supercritical Fluid

Supercritical fluids (SCF) exhibit properties intermediate between those of gases and liquids. A key feature of a SCF is that the fluid density can be varied continuously from liquid-like to gas-like densities by varying either the temperature or pressure, or a combination thereof. Various density-dependent physical properties likewise exhibit similar continuous variation in this region. Some of these properties include, but are not limited to, solvent strength (as evidenced by the solubilities of various substances in the SCF media), polarity, viscosity, diffusivity, heat capacity, thermal conductivity, isothermal compressibility, expandability, contractibility, fluidity, and molecular packing. The density variation in a SCF also influences the chemical potential of solutes and hence, reaction rates and equilibrium constants. Thus, the solvent environment in a SCF media can be optimized for a specific application by tuning the various density-dependent fluid properties.

A fluid is in the SCF state when the system temperature and pressure exceed the corresponding critical point values defined by the critical temperature ($T_c$) and pressure ($P_c$). For pure substances, the $T_c$ and $P_c$ are the highest at which vapor and liquid phases can coexist. Above the $T_c$, a liquid does not form for a pure substance, regardless of the applied pressure. Similarly, the $P_c$ and critical molar volume are defined at this $T_c$ corresponding to the state at which the vapor and liquid phases merge. For carbon dioxide, the critical point is 7.38 MPa ($P_c$) at 31.1° C. ($T_c$). For a discussion of supercritical fluids, see *Kirk-Othmer Encycl. of Chem. Technology*, 4$^{th}$ Ed., Vol. 23, pg. 452-477.

Perfluoropolyethers

Perfluoropolyethers are oligomers or polymers composed of perfluoroalkyl ether repeating units. A perfluoropolyether is typically polydisperse, a mixture of oligomers or polymers with different molecular weights. Perfluoropolyether is synonymous to perfluoropolyalkylether. Other synonymous terms frequently used include "PFPE", "PFAE", "PFPE oil", "PFPE fluid", and "PFPAE". These synonyms can be used interchangeably in this disclosure. The two end groups of a suitable perfluoropolyether for the processes of this invention, independently, can be functionalized or unfunctionalized. In an unfunctionalized perfluoropolyether, the end group can be branched or straight chain perfluoroalkyl radical end groups. Examples of such perfluoropolyethers can have the formula of $C_{r'}F_{(2r'+1)}$-A-$C_{r'}F_{(2r'+1)}$ in which each r' is independently 3 to 6; A can be O—(CF(CF$_3$)CF$_2$—O)$_{w'}$, O—(CF$_2$—O)$_{x'}$(CF$_2$CF$_2$—O)$_{y'}$, O—(C$_2$F$_4$—O)$_{w'}$, O—(C$_2$F$_4$—O)$_{x'}$(C$_3$F$_6$—O)$_{y'}$, O—(CF(CF$_3$)CF$_2$—O)$_{x'}$(CF$_2$—O)$_{y'}$, O—(CF$_2$CF$_2$CF$_2$—O)$_{w'}$, O—(CF(CF$_3$)CF$_2$—O)$_{x'}$(CF$_2$CF$_2$—O)$_{y'}$(CF$_2$—O)$_{z'}$, or combinations of two or more thereof; preferably A is O—(CF(CF$_3$)CF$_2$—O)$_{w'}$, O—(C$_2$F$_4$—O)$_{w'}$, O—(C$_2$F$_4$—O)$_{x'}$(C$_3$F$_6$—O)$_{y'}$, O—(CF$_2$CF$_2$CF$_2$—O)$_{w'}$, or combinations of two or more thereof; w' is an integer from 4 to 100; x' and y' are each independently an integer from 1 to 100. Specific examples include, but are not limited to, F(CF(CF$_3$)—CF$_2$—O)$_9$—CF$_2$CF$_3$, F(CF(CF$_3$)—CF$_2$—O)$_9$—CF(CF$_3$)$_2$, and combinations thereof. In such PFPEs, up to 30% of the halogen atoms can be halogens other than fluorine, such as, for example, chlorine atoms.

In some embodiments of this invention, the lubricating grease comprises a perfluoropolyether wherein at least one end group of the perfluoropolyether is unfunctionalized. In some embodiments, such an unfunctionalized end group is a branched or straight chain perfluoroalkyl group. In some embodiments, such an unfunctionalized end group is a straight chain perfluoroalkyl group.

The two end groups of a suitable perfluoropolyether for the processes of this invention, independently, can also be functionalized. A typical functionalized end group can be selected from the group consisting of esters, hydroxyls, amines, amides, cyanos, carboxylic acids and sulfonic acids. In some embodiments of this invention, these functionalized perfluoropolyethers are added to the fully inert PFPE fluids as anti-corrosion, anti-wear, or extreme pressure additives in an amount of no more than about 10 wt %, and in some embodiments no more than about 3 wt %, compared to the total amount of PFPE fluid.

Representative perfluoropolyethers suitable for the processes of this invention include KRYTOX® fluids which are available from DuPont and have the formula of CF$_3$—(CF$_2$)$_2$—O—[CF(CF$_3$)—CF$_2$—O]$_{j'}$—R'f. In the formula, j' is an integer from 2-100 and R'f is CF$_2$CF$_3$, a C$_3$ to C$_6$ perfluoroalkyl group, or combinations thereof.

Representative perfluoropolyethers suitable for the processes of this invention also include FOMBLIN® and GALDEN® fluids, available from Ausimont, Milan, Italy and produced by perfluoroolefin photooxidation. For example, FOMBLIN®-Y can have the formula of CF$_3$O[CF$_2$CF(CF$_3$)O]$_m$(CF$_2$O)$_n$—R$_{1f}$ or CF$_3$O[CF$_2$CF(CF$_3$)O]$_{m'}$(CF$_2$CF$_2$O)$_o$(CF$_2$O)$_{n'}$—R$_{1f}$. In the formulae R$_{1f}$ is CF$_3$, C$_2$F$_5$, C$_3$F$_7$, or combinations of two or more thereof; (m+n) is an integer from 8-45; and m/n is from 20-1000; o' is 1; (m'+n'+o') is an integer from 8-45; m'/n' is from 20-1000. FOMBLIN®-Z can have the formula of CF$_3$O(CF$_2$CF$_2$—O—)$_{p'}$(CF$_2$—O)$_{q'}$CF$_3$ where (p'+q') is an integer from 40-180 and p'/q' is from 0.5-2.

Representative perfluoropolyethers suitable for the processes of this invention also include DEMNUM® fluids, another family of PFPE available from Daikin Industries. It can be produced by sequential oligomerization and fluorination of 2,2,3,3-tetrafluorooxetane, yielding the formula of F—[(CF$_2$)$_3$—O]$_{t'}$—R$_{2f}$ where R$_{2f}$ is CF$_3$, C$_2$F$_5$, or combinations thereof and t' is an integer from 2-200.

Lubricating Grease

A lubricating grease receiving the extraction processes of this invention typically comprises, other than PFPE, one or more thickeners and optionally one or more other additives such as anti-corrosion additives, anti-rust additives, or anti-wear additives. In some embodiments of this invention, the lubricating grease comprises, consists essentially of, or consists of a thickener and a perfluoropolyether. Moreover, prior to the extraction process at least some extraction aid material is added to the lubricating grease to further aid in the extraction process.

Thickeners for a lubricating grease include, but are not limited to, one or more of the following materials: halogenated polymers and co-polymers such as polytetrafluoroethylene (PTFE), fluorinated ethylene propylene (FEP), perfluoroalkoxy (PFA), perfluoro methyl alkoxy (MFA), ethylene tetrafluoroethylene (ETFE), polychlorotrifluoroethylene (PCTFE), ethylene chlorotrifluoroethylene (ECTFE), polyvinylidene fluoride (PVDF), and the like, talc, silica, clay, boron nitride, titanium dioxide, silicon nitride, metal soaps such as lithium soaps, sodium soaps, lithium complex soaps, calcium sulfonates, aluminum soaps, and the like, melamine cyanurate, urea, polyureas, polyurethanes, and polyolefins such as polyethylene. In some embodiments, the silica thickener is a fumed silica. The thickeners can be present in any appropriate molecular weight distributions, particle shapes and sizes as known to one skilled in the art. For example, the polytetrafluoroethylene thickener can be polytetrafluoroethylene micropowder.

In some embodiments of this invention, the thickener is a halogenated polymer or co-polymer. In some embodiments of this invention, the thickener is selected from the group consisting of PTFE, FEP, PFA, MFA, ETFE, PCTFE, ECTFE, PVDF, and combinations thereof. In some embodiments of this invention, the thickener is PTFE.

In some embodiments of this invention, the thickener is an inorganic compound. In some embodiments of this invention, the thickener is selected from the group consisting of talc, silica, clay, boron nitride, titanium dioxide, silicon nitride, and combinations thereof.

In some embodiments of this invention, the thickener is an organic compound. In some embodiments of this invention, the thickener is selected from the group consisting of metal soaps, melamine cyanurate, urea, polyureas, polyurethanes, polyolefins, and combinations thereof.

In some embodiments of this invention, the metal soap is selected from the group consisting of lithium soaps, sodium soaps, lithium complex soaps, calcium sulfonates, aluminum soaps, and combinations thereof.

In some embodiments of this invention, the lubricating grease further comprises, other than PFPE and thickener, one or more other additives such as anti-corrosion additives, anti-rust additives, or anti-wear additives. Examples of such other additives include sodium nitrite and organic phosphorus compounds.

Extraction Aid Material

The lubricating grease also comprises a suitable extraction aid material which can be added to the lubricating grease in any suitable manner. Extraction aid materials are inert and specific examples include, for example, diatomaceous earth, perlite and cellulose materials. Diatomaceous earth is mined and available in different grades, any of which may find utility according to the present invention. Perlite is a naturally occurring glassy volcanic rock which can also be obtained in various grades. Both Diatomaceous earth and perlite are silica based materials. Cellulose can be defined as a polysaccharide consisting of long unbranched chains of linked glucose units.

The extraction aid material can be provided in any suitable physical form such as particles, powder or fiber form. However, it is preferred that the extraction aid material have an length to diameter aspect ratio of at least about 2:1. In some embodiments of this invention the extraction aid material comprises at least one material selected from the group consisting of fibers, fibrils, filaments, string, thread, wire, and yarn. In some embodiments of this invention the extraction aid material comprises at least one of these materials having an length to diameter aspect ratio of at least about 2:1.

Extraction and Recovery

The present disclosure provides a process for extracting a perfluoropolyether. The process comprises: (a) contacting a solvent comprising a liquid or supercritical carbon dioxide with a lubricating grease comprising a thickener, extraction aid material, and the perfluoropolyether in an extraction zone to form an extraction solution comprising an extracted perfluoropolyether; and (b) recovering the extracted perfluoropolyether from the extraction solution; wherein the recovered extracted perfluoropolyether comprises no more than about 2 wt % of the thickener.

It was found through experiments that perfluoropolyethers contained in a lubricating grease can be efficiently separated and recovered from the grease by using liquid or supercritical carbon dioxide as the extracting solvent and by adding at least some extraction aid material to the grease prior to contacting the liquid or supercritical carbon dioxide and the grease. The process is cost-effective and environmentally friendly.

In some embodiments of this invention, the yield of the extracted perfluoropolyether is at least about 75 wt %. In some embodiments, the yield of the extracted perfluoropolyether is at least about 80 wt %. In some embodiments, the yield of the extracted perfluoropolyether is at least about 85 wt %. In some embodiments, the yield of the extracted perfluoropolyether is at least about 90 wt %. In some embodiments, the yield of the extracted perfluoropolyether is at least about 95 wt %. In some embodiments, the yield of the extracted perfluoropolyether is at least about 99 wt %.

A suitable solvent for the extraction processes of this invention comprises, consists essentially of, or consists of a liquid carbon dioxide or a supercritical carbon dioxide.

In some embodiments of this invention, the solvent comprises, consists essentially of, or consists of a liquid carbon dioxide. In some embodiments, the solvent consists essentially of a liquid carbon dioxide.

In some embodiments of this invention, the solvent comprises, consists essentially of, or consists of a supercritical carbon dioxide. In some embodiments, the solvent consists essentially of a supercritical carbon dioxide.

In some embodiments of this invention, the weight ratio of the solvent to the lubricating grease is no more than about 50. In some embodiments of this invention, the weight ratio of the solvent to the lubricating grease is no more than about 30. In some embodiments, the weight ratio of the solvent to the lubricating grease is no more than about 10. In some embodiments, the weight ratio of the solvent to the lubricating grease is no more than about 8. In some embodiments, the weight ratio of the solvent to the lubricating grease is no more than about 7. In some embodiments, the weight ratio of the solvent to the lubricating grease is no more than about 6. In some embodiments, the weight ratio of the solvent to the lubricating grease is no more than about 5.

In some embodiments of this invention, the weight ratio of the solvent to the lubricating grease is no more than about 7, and the yield of the extracted perfluoropolyether is at least about 75 wt %, at least about 90 wt %, or at least about 95 wt %. In some embodiments of this invention, the solvent comprises, consists essentially of, or consists of a supercritical carbon dioxide, the weight ratio of the solvent to the lubricating grease is no more than about 7, the temperature in the extraction zone is from about 40° C. to about 100° C., the pressure in the extraction zone is from about 2200 psig to about 6000 psig, and the yield of the extracted perfluoropolyether is at least about 90 wt % or at least about 95 wt %.

In some embodiments of this invention, the weight ratio of the lubricating grease to the extraction aid material is from about 10:1 to about 1:10. In some embodiments of this invention, the weight ratio of the lubricating grease to the extraction aid material is from about 3:1 to about 1:3.

The contacting step (a) can be carried out using well-known chemical engineering practices in an extraction vessel. In some embodiments of this invention, a lubricating grease and extraction aid is placed in a container through which the liquid or supercritical carbon dioxide is passed to solubilize the PFPE contained in the lubricating grease to form an extraction solution. The liquid or supercritical carbon dioxide can flow through the lubricating grease continuously, or be exposed to the lubricating grease in a discontinuous batch process.

The extraction vessel can be made of materials known in the art. In some embodiments of this invention, the extraction vessel is a stainless steel, high pressure vessel. In some embodiments of this invention, the extraction vessel is a vertical column and is operated in an upflow or downflow configuration. In some embodiments, the solvent is fed to the extraction zone in an upflow mode. In some embodiments, the solvent is fed to the extraction zone in a downflow mode.

The temperature and pressure in the extraction zone are chosen to keep the carbon dioxide in the liquid or supercritical state during the extraction process.

When the solvent comprises, consists essentially of, or consists of a supercritical carbon dioxide, typically the temperature in the extraction zone is from $T_c$ to no more than about 150° C. In some embodiments, the temperature is from about 40° C. to about 110° C. In some embodiments, the temperature is from about 50° C. to about 100° C. In some embodiments, the temperature is from about 60° C. to about 90° C. In some embodiments, the temperature is from about 70° C. to about 90° C. Typically, the pressure in the extraction zone is from about 1500 psig to about 10,000 psig. In some embodiments, the pressure is from about 1500 psig to about 6000 psig. In some embodiments, the pressure is from about 2000 psig to about 6000 psig. In some embodiments, the pressure is from about 3000 psig to about 5000 psig. In some embodiments, the pressure is from about 4000 psig to about 5000 psig.

When the solvent comprises, consists essentially of, or consists of a liquid carbon dioxide, typically the temperature in the extraction zone is from about 0° C. to less than $T_c$. In some embodiments, the temperature is from about 15° C. to less than $T_c$. In some embodiments, the temperature is from about 25° C. to less than $T_c$.

The extraction solution obtained from the contacting step typically comprises the solvent (i.e., liquid or supercritical carbon dioxide), the extracted perfluoropolyether, extraction aid material, water, and the thickener contaminant.

In the recovering step (b), the extracted perfluoropolyether can be recovered from the extraction solution. In some embodiments of this invention, the extracted perfluoropolyether is recovered from the extraction solution by evaporating the liquid or supercritical carbon dioxide. As the liquid or supercritical carbon dioxide evaporates, the extracted perfluoropolyether is typically precipitated out together with water, extraction aid material, and the thickener contaminant contained in the extraction solution.

It was found through experiments that PFPE can be effectively separated from the lubricating grease substantially free of thickeners and other additives. In some embodiments of this invention, the recovered extracted perfluoropolyether comprises no more than about 2 wt % of the thickener. In some embodiments of this invention, the recovered extracted perfluoropolyether comprises no more than about 1 wt % of the thickener. In some embodiments of this invention, the recovered extracted perfluoropolyether comprises no more than about 0.1 wt % of the thickener. In this disclosure, the sentence "recovered extracted perfluoropolyether comprises no more than about 2 wt % of the thickener" means that the amount of the thickener contaminant contained in the recovered extracted perfluoropolyether is no more than about 2 wt % compared to the total amount of the pure perfluoropolyether and the thickener contained in the recovered extracted perfluoropolyether.

In some embodiments of this invention, the extraction solution is directed through a pressure reduction valve to a separation vessel where the liquid or supercritical carbon dioxide is evaporated and removed and the extracted perfluoropolyether is precipitated from the extraction solution for collection. The relatively pure $CO_2$ stream from the top of the separation vessel may be recycled back to the extraction zone.

In some embodiments of this invention, the recovered extracted perfluoropolyethers can be further purified as described in this disclosure.

Purification

Water and other contaminants in the recovered extracted perfluoropolyether can be removed by techniques known in the art. In some embodiments, water and the extracted perfluoropolyether will separate into two phases, and water can be removed by, for example, simple decantation. In some embodiments, water can be removed by drying agents such as molecular sieves.

In some embodiments of this invention, the recovered extracted perfluoropolyether can be purified by contacting with an adsorbing agent, such as activated carbon, diatomaceous earth, or alumina, to remove the discoloration contaminants. The activated carbon can be in the form of powder, granules, or pellets, et al. Commercially available diatomaceous earth include those sold under the Celite® trademark name.

Activated carbon used in the embodiments of this invention may come from any of the following sources: wood, peat, coal, coconut shells, bones, lignite, petroleum-based residues and sugar. Commercially available activated carbons which may be used include those sold under the following trademarks: Barneby & Sutcliffe™, Darco™, Nucharm, Columbia JXN™, Columbia LCK™, Calgon™ PCB, Calgon™ BPL, Westvaco™, Norit™, Takeda™ and Barnaby Cheny NB™.

The activated carbon also includes three dimensional matrix porous carbonaceous materials. Examples are those described in U.S. Pat. No. 4,978,649. In one embodiment of the invention, activated carbon includes three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

In some embodiments, the purified extracted perfluoropolyether can be fractionated or distilled to generate perfluoropolyether with desired molecular weight. The purified extracted perfluoropolyether can also undergo chemical reactions to produce PFPE oil with desired properties.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Materials:

Twelve grades of formulated perflurorpolyether lubricating greases and a mixture of various waste greases were used in these examples, including commercially-available DuPont Krytox® greases and non-commercial research samples to illustrate the breadth of the applicability of this extraction process at recovering perfluoropolyether oil from various grease matrix formulations.

Krytox® GPL 203: 15-45% PTFE Micropowder and 55-85% PFPE Oil
Krytox® GPL 207: 15-45% PTFE Micropowder and 55-85% PFPE Oil
Krytox® GPL 227: 18-27% PTFE Micropowder, 1-5% Sodium Nitrite and 71-80% PFPE Oil
Krytox® GPL226SR: 23-25% PTFE Micropowder, 2-3% of a proprietary additive, and 73-74% PFPE oil
Krytox® NRT 8908: 30-50% Talc ($Mg_3H_2(SiO_3)_4$) and 50-70% PFPE oil
Krytox® GPL 407: 1-10% Silica and 90-95% PFPE Oil
XHT-BD: 15-25% Boron Nitride, and 75-85% PFPE oil
Mg Stearate: GPL205: 15-45% Mg Stearate powder and 55-85% PFPE oil
BN/PTFE: GPL205: 10-40% Micropowder consisting of 50 wt % Boron Nitride/50 wt % PTFE thickener and 6-85% PFPE oil
PU: 15-45% Polyurea thickener and 35-45% PFPE oil
PU/ZnO: 15-45% Polyurea+zinc oxide thickener and 35-45% PFPE oil
GPL 226 GRS: 23-25% PTFE Micropowder, 2-3% of a proprietary additive, and 73-74% PFPE oil Carbon dioxide (99.99% grade) was obtained from standard suppliers, such as GTS-Welco.

Extraction Method:

The lab- and pilot-scale extraction examples were conducted using a custom high-pressure extraction apparatus illustrated in FIG. 1. The 300 mL and 7 L extraction vessels (High Pressure Equipment Co.) were fabricated from 316 SS and were equipped with a 2-micron sintered metal filter on the effluent end of the vessel. The 300 mL extraction vessel was fitted with band heating elements (Power Modules, Inc.), and the 7 L extraction vessel was wrapped with heating tape. Both heating sources were controlled by an automated temperature controller, and the vessels and heating sources were equipped with insulation to maintain a uniform extraction temperature. The $CO_2$ was supplied from a standard cylinder with the $CO_2$ vapor from the top of the cylinder condensed and chilled to approximately 5° C. in a heat exchanger and fed into one of two positive displacement syringe pumps (Isco Model 100D/X, interconnected via a dual-pump Model DP VK valve kit and operated in continuous flow mode) for metering into the 300 mL extraction vessel, or into a diaphragm compressor (Newport Scientific) for metering into the 7 L extraction vessel. Prior to entering the top of the extraction vessel, the inlet $CO_2$ stream was preheated by an electrical heating tape (Amptek AWH-051) wrapped around the transfer tubing which was operated via an automated temperature controller. The extraction temperature was monitored and controlled from thermocouples (Omega Engineering Inc.) located at the extraction vessel inlet. The extraction pressure was maintained with an automated back pressure regulator (Jasco Model BP-1580-81) on the effluent side of the 300 mL vessel, or with a micro-metering valve (Autoclave Engineers, HT-A13537) on the effluent side of the 7 L vessel. The extracted perfluoropolyether oil was collected in a sample vessel while simultaneously venting the $CO_2$ solvent to the atmosphere. The commercial-scale system utilized a similar process flowsheet, except a 320 L stainless steel extraction vessel was used, and the $CO_2$ solvent was recirculated through the extraction vessel. Extracted oil samples were collected from a separator vessel located in the solvent recycle loop downstream of a pressure control valve used to reduce the process pressure downstream of the extraction vessel.

For each example, a quantity of the starting lubricating grease was mixed with a designated amount of Cellu-Flo CLR-138 (Gusmer Enterprises) cellulosic fiber which was used as a representative extraction aid. The grease/Cellu-Flo mixture was charged directly into the extraction vessel, and then the system was sealed, heated, and pressurized at the desired $CO_2$ flow rate to the desired operating conditions. The time, pressure, temperature, recovered PFPE oil weight, and total $CO_2$ volume fed were monitored during the extraction. When the desired extraction time was complete, the system pressure was reduced to atmospheric pressure, the extraction vessel was opened, and the residual extracted grease matrix/Cellu-flo mixture was removed from the vessel. Reported extraction yields from the starting lubricating grease samples were determined gravimetrically based on the total amount of PFPE oil contained in the starting lubricating greases.

The following examples show quantitative results for semi-continuous $CO_2$ extractions of the eleven DuPont Krytox® lubricating grease samples under various conditions to exemplify the technical feasibility of this process approach for separating the Krytox® PFPE oil from the lubricating grease matrix. The following examples include Examples 1 and 2 and Comparative Examples 1 and 2 which directly compare extraction results for two of the greases using a cellulose fiber extraction aid incorporated into the grease matrix (Examples 1 and 2) versus extraction without use of the cellulose fiber (Comparative Examples 1 and 2).

EXAMPLES

Example 1 and Comparative Example 1

Extraction Curve at 4500 Psig and 80° C. Using Supercritical $CO_2$ with Krytox® GPL 227 Lubricating Grease The following Examples demonstrate the feasibility of isolating perfluoropolyether oil from a PTFE-based lubricating grease matrix with supercritical $CO_2$ at extraction conditions of 4500 psig and 80° C., comparing results using a cellulose fiber extraction aid incorporated into the grease matrix versus extraction without use of an extraction aid material.

Comparative Example 1

Figure 2:
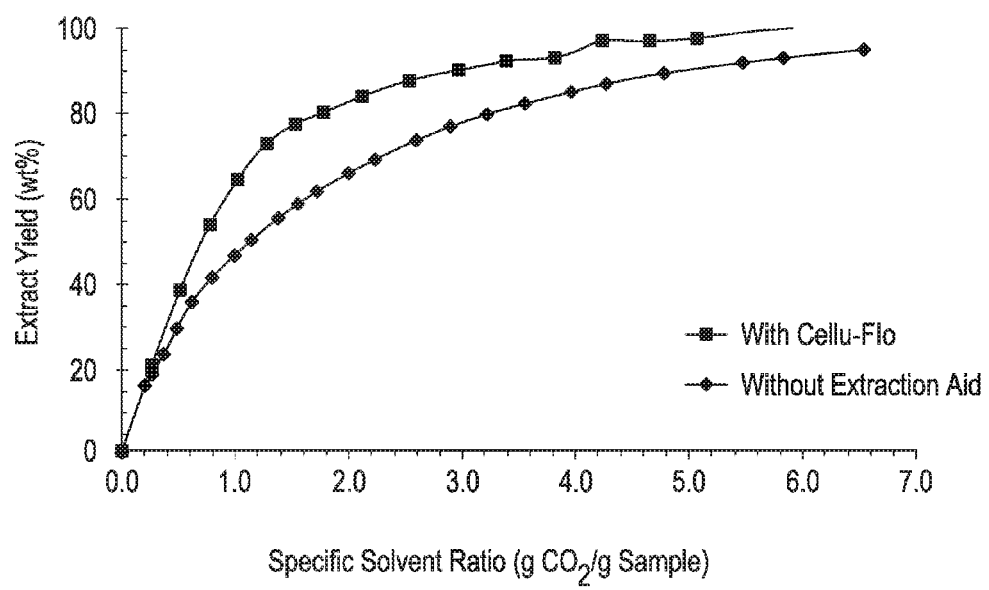
FIG. 2 includes as illustration the extraction curve (extraction yield versus solvent to lubricating grease ratio, or solvent-to-feed ratio) for Example 1 and Comparative Example 1.

A 300 mL extraction vessel was charged with 232.5 g of DuPont Krytox® GPL 227 lubricating grease which was placed in two perforated metal baskets in the vessel. The extraction vessel and lubricating grease sample were flushed with $CO_2$ and then pressurized to 4500 psig with $CO_2$ at 80° C. The lubricating grease sample was extracted at these conditions and a $CO_2$ flow rate of 2.1 g/min for 9 h with intermittent PFPE oil samples collected from the extract. Table 1 shows the corresponding cumulative extraction yield as a function of the cumulative solvent-to-feed ratio, and this trend is further illustrated in FIG. 2. A total of 95.1 wt % of the 183.4 g of PFPE oil in the starting lubricating grease was recovered in the extract with a total cumulative solvent-to-feed ratio of 6.54. FT-IR and $^{19}F$ NMR analysis verified the recovered PFPE oils to be structurally identical to the original PFPE oils in the starting lubricating grease.

TABLE 1

Solvent-to-Feed Ratio and Extraction Yield Data at 4500 psig and 80° C. for Comparative Example 1 with No Extraction Aid

| Specific Solvent Ratio (g $CO_2$/g Lubricating Grease) | Extraction Yield (wt %) |
| --- | --- |
| 0.20 | 16.1 |
| 0.37 | 23.4 |
| 0.62 | 35.8 |
| 1.15 | 50.6 |
| 1.71 | 61.7 |
| 2.24 | 69.5 |
| 2.90 | 77.2 |
| 3.55 | 82.6 |
| 4.27 | 87.1 |
| 5.48 | 92.1 |
| 6.54 | 95.1 |

Example 1

A 300 mL extraction vessel was charged with 61.2 g of a well-mixed lubricating grease sample comprised of 15.8 g of DuPont Krytox® GPL 227 lubricating grease and 45.4 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 1.8 h with intermittent PFPE oil samples collected from the extract. Table 2 shows the corresponding cumulative extraction yield as a function of the cumulative solvent-to-feed ratio, and this trend is further illustrated in FIG. 2. The 12.4 g of PFPE oil in the starting lubricating grease was recovered quantitatively in the extract with a total cumulative solvent-to-feed ratio of 8.5. FT-IR analysis verified the recovered PFPE oils to be structurally identical to the original PFPE oils in the starting lubricating grease.

TABLE 2

Solvent-to-Feed Ratio and Extraction Yield Data at 4500 psig and 80° C. for Example 1 with Extraction Aid

| Specific Solvent Ratio (g $CO_2$/g Lubricating Grease/Cellu-Flo) | Extraction Yield (wt %) |
| --- | --- |
| 0.25 | 20.8 |
| 0.51 | 38.7 |
| 0.76 | 53.7 |
| 1.02 | 64.8 |
| 1.52 | 77.5 |
| 2.11 | 84.2 |
| 2.96 | 90.5 |
| 3.81 | 93.2 |
| 4.65 | 97.3 |
| 5.92 | 100.4 |
| 8.46 | 101.0 |

Example 2 and Comparative Example 2

Extraction Curve at 4500 Psig and 80° C. Using Supercritical $CO_2$ with Krytox® GPL 407 Lubricating Grease The following Examples demonstrate the feasibility of isolating perfluoropolyether oil from a silica-based lubricating grease matrix with supercritical $CO_2$ at extraction conditions of 4500 psig and 80° C., comparing results using a cellulose fiber extraction aid incorporated into the grease matrix versus extraction without use of an extraction aid.

Comparative Example 2

Figure 3:
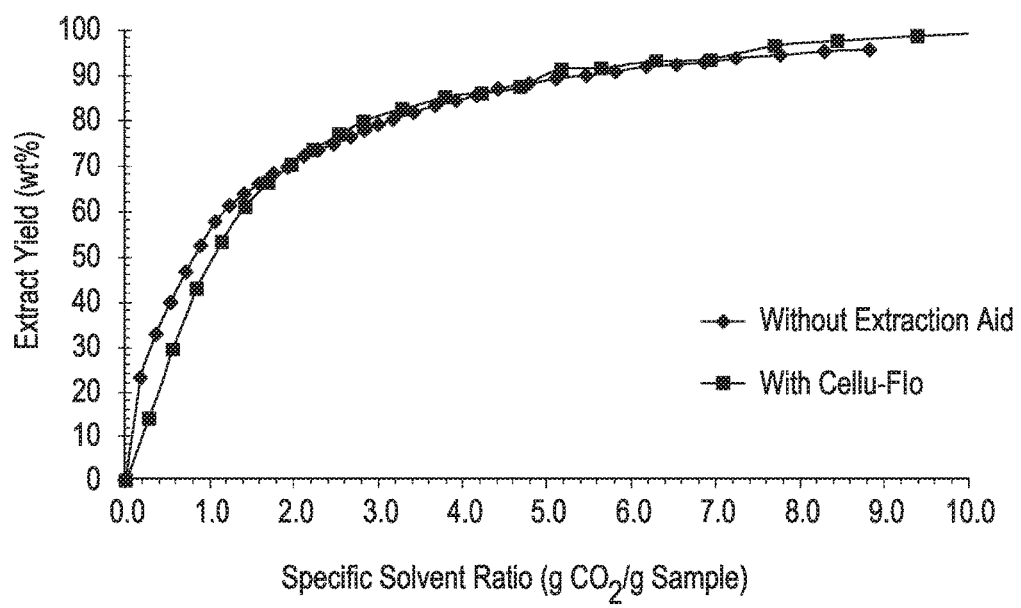
FIG. 3 includes as illustration the extraction curve (extraction yield versus solvent to lubricating grease ratio, or solvent-to-feed ratio) for Example 2 and Comparative Example 2.

A 300 mL extraction vessel was charged with 146.7 g of DuPont Krytox® GPL 407 lubricating grease which was placed in two perforated metal baskets in the vessel. The extraction vessel and lubricating grease sample were flushed with $CO_2$ and then pressurized to 4500 psig with $CO_2$ at 80° C. The lubricating grease sample was extracted at these conditions and a $CO_2$ flow rate of 5.2 g/min for 4.2 h with intermittent PFPE oil samples collected from the extract. Table 3 shows the corresponding cumulative extraction yield as a function of the cumulative solvent-to-feed ratio, and this trend is further illustrated in FIG. 3. A total of 97.2 wt % of the 139.74 g of PFPE oil in the starting lubricating grease was recovered in the extract with a total cumulative solvent-to-feed ratio of 8.8. FT-IR analysis verified the recovered PFPE oils to be structurally identical to the original PFPE oils in the starting lubricating grease.

TABLE 3

Solvent-to-Feed Ratio and Extraction Yield Data at 4500 psig and 80° C. for Comparative Example 2 with No Extraction Aid

| Specific Solvent Ratio (g $CO_2$/g Lubricating Grease) | Extraction Yield (wt %) |
| --- | --- |
| 0.17 | 23.2 |
| 0.35 | 32.8 |
| 0.53 | 39.9 |
| 0.88 | 52.2 |
| 1.23 | 61.5 |
| 1.76 | 68.2 |
| 2.29 | 73.5 |
| 3.00 | 79.3 |
| 4.16 | 85.6 |
| 5.47 | 90.1 |
| 6.53 | 92.6 |

TABLE 3-continued

Solvent-to-Feed Ratio and Extraction Yield Data at 4500 psig
and 80° C. for Comparative Example 2 with No Extraction Aid

| Specific Solvent Ratio (g $CO_2$/g Lubricating Grease) | Extraction Yield (wt %) |
|---|---|
| 7.24 | 93.9 |
| 8.82 | 97.2 |

Example 2

A 300 mL extraction vessel was charged with 55.1 g of a well-mixed lubricating grease sample comprised of 13.9 g of DuPont Krytox® GPL 407 lubricating grease and 41.2 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 1.8 h with intermittent PFPE oil samples collected from the extract. Table 4 shows the corresponding cumulative extraction yield as a function of the cumulative solvent-to-feed ratio, and this trend is further illustrated in FIG. 3. The 13.2 g of PFPE oil in the starting lubricating grease was recovered quantitatively in the extract with a total cumulative solvent-to-feed ratio of 10.3. FT-IR analysis verified the recovered PFPE oils to be structurally identical to the original PFPE oils in the starting lubricating grease.

TABLE 4

Solvent-to-Feed Ratio and Extraction Yield Data at 4500 psig and 80° C. for Example 2 with Extraction Aid

| Specific Solvent Ratio (g $CO_2$/g Lubricating Grease/Cellu-Flo)) | Extraction Yield (wt %) |
|---|---|
| 0.28 | 14.5 |
| 0.56 | 29.7 |
| 0.84 | 42.8 |
| 1.12 | 53.2 |
| 1.69 | 66.3 |
| 2.25 | 73.7 |
| 2.82 | 79.7 |
| 3.75 | 85.2 |
| 4.69 | 87.5 |
| 5.63 | 91.6 |
| 6.94 | 93.3 |
| 8.45 | 97.7 |
| 10.3 | 100.0 |

Example 3

Extraction Curve at 4500 Psig and 80° C. Using Supercritical $CO_2$ with Krytox® NRT 8908 Lubricating Grease This Example demonstrates the feasibility of isolating perfluoropolyether oil from a talc-based lubricating grease matrix with supercritical $CO_2$ at extraction conditions of 4500 psig and 80° C.

A 300 mL extraction vessel was charged with 50.8 g of a well-mixed lubricating grease sample comprised of 12.3 g of DuPont Krytox® GPL 407 lubricating grease and 38.5 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 2.4 h with intermittent PFPE oil samples collected from the extract. Table 5 shows the corresponding cumulative extraction yield as a function of the cumulative solvent-to-feed ratio. The 8.6 g of PFPE oil in the starting lubricating grease was recovered quantitatively in the extract with a total cumulative solvent-to-feed ratio of 12.22. FT-IR analysis verified the recovered PFPE oils to be structurally identical to the original PFPE oils in the starting lubricating grease.

TABLE 5

Solvent-to-Feed Ratio and Extraction Yield Data at 4500 psig and 80° C. for Example 3

| Specific Solvent Ratio (g $CO_2$/g Lubricating Grease/Cellu-Flo) | Extraction Yield (wt %) |
|---|---|
| 0.31 | 16.9 |
| 0.61 | 30.7 |
| 0.92 | 42.3 |
| 1.22 | 48.7 |
| 1.83 | 57.1 |
| 2.44 | 63.4 |
| 3.36 | 71.6 |
| 4.48 | 78.8 |
| 5.60 | 84.3 |
| 7.13 | 91.6 |
| 8.35 | 96.4 |
| 10.19 | 97.6 |
| 12.22 | 100.0 |

Example 4

Extraction Curve at 4500 Psig and 80° C. Using Supercritical $CO_2$ with Krytox® GPL 226SR Lubricating Grease This Example demonstrates the feasibility of isolating perfluoropolyether oil from a PTFE Micropowder-based lubricating grease matrix containing SP3 additive with supercritical $CO_2$ at extraction conditions of 4500 psig and 80° C.

A 300 mL extraction vessel was charged with 54.6 g of a well-mixed lubricating grease sample comprised of 12.6 g of DuPont Krytox® GPL 226SR lubricating grease and 41.9 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 1.8 h with intermittent PFPE oil samples collected from the extract. Table 6 shows the corresponding cumulative extraction yield as a function of the cumulative solvent-to-feed ratio. The 9.5 g of PFPE oil in the starting lubricating grease was recovered quantitatively in the extract with a total cumulative solvent-to-feed ratio of 7.8. FT-IR analysis verified the recovered PFPE oils to be structurally identical to the original PFPE oils in the starting lubricating grease.

TABLE 6

Solvent-to-Feed Ratio and Extraction Yield Data
at 4500 psig and 80° C. for Example 4

| Specific Solvent Ratio (g $CO_2$/g Lubricating Grease/Cellu-Flo) | Extraction Yield (wt %) |
|---|---|
| 0.28 | 16.3 |
| 0.57 | 32.4 |
| 0.85 | 44.9 |
| 1.14 | 53.8 |
| 1.71 | 63.5 |
| 2.56 | 74.6 |
| 3.32 | 81.2 |
| 4.27 | 87.7 |
| 5.21 | 91.8 |
| 6.35 | 94.5 |
| 7.02 | 95.9 |
| 7.77 | 100.8 |

Example 5

Extraction Curve at 4500 Psig and 80° C. Using Supercritical $CO_2$ with Krytox® XHT-BD Lubricating Grease This Example demonstrates the feasibility of isolating perfluoropolyether oil from a Boron Nitride-based lubricating grease matrix with supercritical $CO_2$ at extraction conditions of 4500 psig and 80° C.

A 300 mL extraction vessel was charged with 58.4 g of a well-mixed lubricating grease sample comprised of 14.6 g of DuPont Krytox® XHT-BD lubricating grease and 43.8 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 1.8 h with intermittent PFPE oil samples collected from the extract. Table 7 shows the corresponding cumulative extraction yield as a function of the cumulative solvent-to-feed ratio. The 11.4 g of PFPE oil in the starting lubricating grease was recovered quantitatively in the extract with a total cumulative solvent-to-feed ratio of 9.7. FT-IR analysis verified the recovered PFPE oils to be structurally identical to the original PFPE oils in the starting lubricating grease.

TABLE 7

Solvent-to-Feed Ratio and Extraction Yield
Data at 4500 psig and 80° C. for Example 5

| Specific Solvent Ratio (g $CO_2$/g Lubricating Grease/Cellu-Flo) | Extraction Yield (wt %) |
|---|---|
| 0.27 | 13.6 |
| 0.53 | 27.7 |
| 0.80 | 40.6 |
| 1.33 | 56.7 |
| 1.86 | 65.0 |
| 2.66 | 74.1 |
| 3.55 | 80.8 |
| 4.43 | 85.5 |
| 5.32 | 89.7 |
| 6.56 | 94.7 |
| 7.98 | 98.2 |
| 8.86 | 98.9 |
| 9.75 | 101.3 |

Example 6

Extraction Curve at 4500 Psig and 80° C. Using Supercritical $CO_2$ with Magnesium Stearate-Thickened Krytox® GPL205 Lubricating Grease This Example demonstrates the feasibility of isolating perfluoropolyether oil from a Magnesium Stearate-based lubricating grease matrix with supercritical $CO_2$ at extraction conditions of 4500 psig and 80° C.

A 300 mL extraction vessel was charged with 45.8 g of a well-mixed lubricating grease sample comprised of 11.3 g of Magnesium Stearate-thickened DuPont Krytox® GPL205 PFPE oil and 34.7 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 1.6 g/min for 2.6 h with intermittent PFPE oil samples collected from the extract. Table 8 shows the corresponding cumulative extraction yield as a function of the cumulative solvent-to-feed ratio. A total of 89.4 wt % of the 9.1 g of PFPE oil in the starting lubricating grease was recovered in the extract with a total cumulative solvent-to-feed ratio of 5.3. FT-IR analysis verified the recovered PFPE oils to be structurally identical to the original PFPE oils in the starting lubricating grease.

TABLE 8

Solvent-to-Feed Ratio and Extraction Yield
Data at 4500 psig and 80° C. for Example 6

| Specific Solvent Ratio (g $CO_2$/g Lubricating Grease/Cellu-Flo) | Extraction Yield (wt %) |
|---|---|
| 0.17 | 8.7 |
| 0.34 | 16.1 |
| 0.51 | 24.6 |
| 0.68 | 31.3 |
| 1.02 | 36.2 |
| 1.69 | 46.5 |
| 2.37 | 53.5 |
| 3.39 | 65.1 |
| 4.40 | 74.3 |
| 5.25 | 89.4 |

Example 7

Extraction Curve at 4500 Psig and 80° C. Using Supercritical $CO_2$ with 50 wt % Boron Nitride/50 wt % PTFE Micropowder-Thickened Krytox® GPL205 Lubricating Grease This Example demonstrated the feasibility of isolating perfluoropolyether oil from a Boron Nitride/PTFE-based lubricating grease matrix with supercritical $CO_2$ at extraction conditions of 4500 psig and 80° C.

A 300 mL extraction vessel was charged with 54.5 g of a well-mixed lubricating grease sample comprised of 13.7 g of Boron Nitride, PTFE Micropowder and DuPont Krytox® GPL205 PFPE oil and 40.8 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 2.3 h with intermittent PFPE oil samples collected from the extract. Table 9 shows the corresponding cumulative extraction yield as a function of the cumulative solvent-to-feed ratio. A total of 95.7 wt % of the 11.2 g of PFPE oil in the starting lubricating grease was recovered in the extract with a total cumulative solvent-to-feed ratio of 13.3. FT-IR analysis verified the recovered PFPE oils to be structurally identical to the original PFPE oils in the starting lubricating grease.

TABLE 9

Solvent-to-Feed Ratio and Extraction Yield Data at 4500 psig and 80° C. for Example 7

| Specific Solvent Ratio (g $CO_2$/g Lubricating Grease/Cellu-Flo) | Extraction Yield (wt %) |
|---|---|
| 0.28 | 15.8 |
| 0.57 | 29.2 |
| 0.85 | 37.6 |
| 1.14 | 42.7 |
| 1.71 | 49.8 |
| 2.56 | 58.8 |
| 3.80 | 69.2 |
| 5.22 | 76.7 |
| 7.02 | 83.7 |
| 9.49 | 90.3 |
| 11.39 | 93.0 |
| 13.28 | 95.7 |

Example 8

Extraction Curve at 4500 Psig and 80° C. Using Supercritical $CO_2$ with Lubricating Grease Comprised of Polyurea Thickener with Both a Polyester and Krytox® 1531 PFPE Oil This Example demonstrated the feasibility of isolating a polyester and a perfluoropolyether oil from a polyurea-based lubricating grease matrix with supercritical $CO_2$ at extraction conditions of 4500 psig and 80° C.

A 300 mL extraction vessel was charged with 58.4 g of a well-mixed lubricating grease sample comprised of 14.6 g of polyurea and a combination of a polyester and DuPont Krytox® 1531 PFPE oil and 43.8 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 1.5 h with intermittent PFPE oil samples collected from the extract. Table 10 shows the corresponding cumulative extraction yield as a function of the cumulative solvent-to-feed ratio. The 9.6 g of polyester and PFPE oil in the starting lubricating grease was recovered quantitatively in the extract with a total cumulative solvent-to-feed ratio of 5.3. FT-IR analysis verified the recovered PFPE oils to be structurally identical to the original PFPE oils in the starting lubricating grease.

TABLE 10

Solvent-to-Feed Ratio and Extraction Yield Data at 4500 psig and 80° C. for Example 8

| Specific Solvent Ratio (g $CO_2$/g Lubricating Grease/Cellu-Flo) | Extraction Yield (wt %) |
|---|---|
| 0.27 | 13.1 |
| 0.53 | 25.0 |
| 0.80 | 36.0 |
| 1.33 | 53.2 |
| 1.86 | 66.0 |
| 2.39 | 75.5 |
| 2.66 | 79.4 |
| 3.55 | 88.1 |
| 4.43 | 95.7 |
| 5.32 | 100.1 |

Example 9

Extraction Curve at 4500 Psig and 80° C. Using Supercritical $CO_2$ with Lubricating Grease Comprised of Polyurea/Zinc Oxide Thickener with Both a Polyester and Krytox® 1531 PFPE Oil This Example demonstrates the feasibility of isolating a polyester and a perfluoropolyether oil from a polyurea and zinc oxide-based lubricating grease matrix with supercritical $CO_2$ at extraction conditions of 4500 psig and 80° C.

A 300 mL extraction vessel was charged with 55.4 g of a well-mixed lubricating grease sample comprised of 13.9 g of polyurea, zinc oxide, and a combination of a polyester and DuPont Krytox® 1531 PFPE oil and 41.4 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 1.5 h with intermittent PFPE oil samples collected from the extract. Table 11 shows the corresponding cumulative extraction yield as a function of the cumulative solvent-to-feed ratio. A total of 97.2 wt % of the 8.6 g of polyester and PFPE oil in the starting lubricating grease was recovered in the extract with a total cumulative solvent-to-feed ratio of 8.4. FT-IR analysis verified the recovered PFPE oils to be structurally identical to the original PFPE oils in the starting lubricating grease.

TABLE 11

Solvent-to-Feed Ratio and Extraction Yield Data at 4500 psig and 80° C. for Example 9

| Specific Solvent Ratio (g $CO_2$/g Lubricating Grease/Cellu-Flo) | Extraction Yield (wt %) |
|---|---|
| 0.28 | 7.3 |
| 0.56 | 17.2 |
| 0.84 | 26.9 |
| 1.12 | 35.3 |
| 1.68 | 49.2 |
| 2.24 | 59.8 |
| 2.80 | 67.5 |
| 3.74 | 76.5 |
| 4.67 | 83.1 |
| 5.61 | 88.0 |
| 6.92 | 91.7 |
| 8.41 | 97.2 |

Example 10

Extraction Curve at 4500 Psig and 80° C. Using Supercritical $CO_2$ with Krytox® GPL 207 Lubricating Grease This Example demonstrates the feasibility of isolating a polyester and a perfluoropolyether oil from a PTFE-based lubricating grease matrix with supercritical $CO_2$ at extraction conditions of 4500 psig and 80° C.

A 300 mL extraction vessel was charged with 59.2 g of a well-mixed lubricating grease sample comprised of 15.1 g of Krytox® GPL 207 grease and 44.2 g of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 80° C. The grease/Cellu-Flo sample was then extracted at these conditions and a $CO_2$ flow rate of 5.2 g/min for 2.5 h with intermittent PFPE oil samples collected from the extract. Table 12 shows the corresponding cumulative extraction yield as a function of the cumulative solvent-to-feed ratio. A total of 99.2 wt % of the 11.9 g of PFPE oil in the starting lubricating grease was recovered in the extract with a total cumulative solvent-to-feed ratio of 13.1. FT-IR analysis verified the recovered PFPE oils to be structurally identical to the original PFPE oils in the starting lubricating grease.

TABLE 12

Solvent-to-Feed Ratio and Extraction Yield Data at 4500 psig and 80° C. for Example 10

| Specific Solvent Ratio (g $CO_2$/g Lubricating Grease/Cellu-Flo) | Extraction Yield (wt %) |
|---|---|
| 0.26 | 13.2 |
| 0.52 | 25.6 |
| 0.79 | 36.9 |
| 1.05 | 44.3 |
| 1.57 | 54.0 |
| 2.19 | 63.1 |
| 3.06 | 72.3 |
| 3.93 | 79.5 |
| 4.81 | 84.1 |
| 5.86 | 88.2 |
| 7.17 | 92.0 |
| 8.74 | 95.6 |
| 10.49 | 96.6 |
| 13.11 | 99.2 |

Example 11

Extraction Curve at 4500 Psig and 60° C. Using Supercritical $CO_2$ with Krytox® GPL 226 GRS Lubricating Grease This Example demonstrates the feasibility of isolating a perfluoropolyether oil from a Sodium Nitrite-inhibited PTFE Micropowder-based lubricating grease matrix with supercritical $CO_2$ at extraction conditions of 4500 psig and 60° C. in a pilot scale (7 L vessel) extraction system.

A 7 L extraction vessel was charged with approximately 4.0 kg of a well-mixed lubricating grease sample comprised of 2.7 kg of Krytox® GPL 226 GRS grease and 1.3 kg of Cellu-Flo CLR-138 cellulose fiber, which was placed directly in the extraction vessel. The extraction vessel and grease/Cellu-flow sample were flushed with $CO_2$ and then pressurized to 4500 psig with $CO_2$ at 60° C. The grease/Cellu-Flo sample was then extracted at these conditions with PFPE oil samples collected from the extract. Table 13 shows the corresponding cumulative extraction yield as a function of the cumulative solvent-to-feed ratio. A total of 98.6 wt % of the 2.1 kg of PFPE oil in the starting lubricating grease was recovered in the extract with a total cumulative solvent-to-feed ratio of 13.1. FT-IR analysis verified the recovered PFPE oils to be structurally identical to the original PFPE oils in the starting lubricating grease.

TABLE 13

Solvent-to-Feed Ratio and Extraction Yield Data at 4500 psig and 60° C. for Example 11

| Specific Solvent Ratio (kg $CO_2$/kg Grease/Cellu-Flo) | Extraction Yield (wt %) |
|---|---|
| 1.3 | 46.1 |
| 5.3 | 84.5 |
| 8.0 | 93.6 |
| 12.0 | 98.5 |
| 13.1 | 98.6 |

Example 12

Extraction Curve at 1500-3500 Psig and 50° C. Using Supercritical $CO_2$ with Mixed Krytox® Lubricating Grease This Example demonstrates the feasibility of isolating a perfluoropolyether oil from a mixed Krytox® lubricating grease matrix with supercritical $CO_2$ at extraction conditions of 50° C. and pressures ranging from 1500-3500 psig in a commercial scale (320 L vessel) extraction system.

A 320 L extraction vessel was charged with approximately 192 kg of a well-mixed lubricating grease sample comprised of 147 kg of mixed Krytox® grease and 45 kg of Cellu-Flo CLR-138 cellulose fiber, which was placed directly in the extraction vessel. The extraction vessel and grease/Cellu-flow sample were flushed with $CO_2$ and then pressurized to 1500 psig with $CO_2$ at 50° C. The grease/Cellu-Flo sample was then extracted with PFPE oil samples collected from the extract. The pressure was gradually increased to 3500 psig over the course of the extraction. Table 14 shows the corresponding cumulative extraction yield as a function of the cumulative solvent-to-feed ratio. A total of approximately 97.2 wt % of the estimated 116 kg of PFPE oil in the starting lubricating grease was recovered in the extract with a total cumulative solvent-to-feed ratio of 21.4. FT-IR analysis verified the recovered PFPE oils to be structurally identical to the original PFPE oils in the starting lubricating grease.

TABLE 14

Solvent-to-Feed Ratio and Extraction Yield Data at 1500-3500 psig and 50° C. for Example 12

| Extraction Pressure (psig) | Specific Solvent Ratio (kg $CO_2$/ kg Grease/Cellu-Flo) | Cumulative Fraction of Grease Charge (wt %) | Approximate Extraction Yield (wt %) |
|---|---|---|---|
| 1500 | 2.0 | 16.8 | 21.3 |
| 2000 | 5.9 | 36.1 | 45.7 |
| 2200 | 7.2 | 43.7 | 55.3 |
| 2500 | 10.0 | 63.9 | 81.0 |
| 2500 | 12.9 | 71.3 | 90.3 |
| 2500 | 15.9 | 74.9 | 94.8 |
| 3000 | 18.9 | 75.9 | 96.1 |
| 3500 | 21.4 | 76.7 | 97.2 |

What is claimed is:

1. A process for extracting a perfluoropolyether from lubricating grease, comprising:
   (a) contacting a solvent comprising a liquid or supercritical carbon dioxide with the lubricating grease, wherein the lubricating grease comprises a thickener, extraction aid material, and the perfluoropolyether in an extraction zone to form an extraction solution comprising an extracted perfluoropolyether and wherein the extracted perfluoropolyether comprises unfunctionalized perfluoropolyether and optionally functionalized perfluoropolyether, the functionalized perfluoropolyether if present being present in an amount of no more than 10 wt % based on the total amount of perfluoropolyether; and
   (b) recovering the extracted perfluoropolyether from the extraction solution; wherein the recovered extracted perfluoropolyether comprises no more than about 2 wt % of the thickener;
   wherein the yield of the extracted perfluoropolyether is at least about 75 wt %.

2. The process of claim 1, wherein the recovered extracted perfluoropolyether comprises no more than about 0.1 wt % of the thickener.

3. The process of claim 1, wherein the thickener is selected from the group consisting of PTFE, FEP, PFA, MFA, ETFE, PCTFE, ECTFE, PVDF, and combinations thereof.

4. The process of claim 3, wherein the thickener is PTFE.

5. The process of claim 1, wherein the thickener is selected from the group consisting of talc, silica, clay, boron nitride, titanium dioxide, silicon nitride, and combinations thereof.

6. The process of claim 1, wherein the thickener is selected from the group consisting of metal soaps, melamine cyanurate, urea, polyureas, polyurethanes, polyolefins, and combinations thereof.

7. The process of claim 6, wherein the metal soap is selected from the group consisting of lithium soaps, sodium soaps, lithium complex soaps, calcium sulfonates, aluminum soaps, and combinations thereof.

8. The process of claim 1, wherein the weight ratio of the solvent to the lubricating grease is no more than about 50.

9. The process of claim 1, wherein the solvent comprises supercritical carbon dioxide.

10. The process of claim 9, wherein the extraction zone has a temperature and wherein the temperature in the extraction zone is from about 40° C. to about 110° C.

11. The process of claim 9, wherein the extraction zone has a temperature and wherein the temperature in the extraction zone is from about 70° C. to about 90° C.

12. The process of claim 9, wherein the extraction zone has a pressure and wherein the pressure in the extraction zone is from about 1500 psig to about 6000 psig.

13. The process of claim 9, wherein the extraction zone has a pressure and wherein the pressure in the extraction zone is from about 4000 psig to about 5000 psig.

14. The process of claim 1, wherein the solvent comprises liquid carbon dioxide.

15. The process of claim 14, wherein the extraction zone has a temperature and wherein the temperature in the extraction zone is from about 25° C. to less than 31.1° C.

16. The process of claim 1, wherein the yield of the extracted perfluoropolyether is at least about 90 wt %.

17. The process of claim 1, wherein the recovered extracted perfluoropolyether is further purified by an adsorbing agent.

18. The process of claim 1, wherein the extraction aid material comprises a material selected from the group consisting of diatomaceous earth, perlite, and cellulose materials.

19. The process of claim 1, wherein the extraction aid material is selected from the group consisting of particles, powders, fibers, fibrils, filaments, string, thread, wire and yarn.

20. The process of claim 1, wherein the weight ratio of the lubricating grease to the extraction aid material is from about 10:1 to about 1:10.

* * * * *